(12) United States Patent
Saitoh et al.

(10) Patent No.: US 8,747,366 B2
(45) Date of Patent: Jun. 10, 2014

(54) MEDICAL NEEDLE (75) Inventors: Hideya Saitoh, Tokyo (JP); Akihiro Saruya, Saitama (JP)

(73) Assignee: Unisis Corporation, Tokyo (JP)

( * ) Notice: Subject to any disclaimer, the term of this patent is extended or adjusted under 35 U.S.C. 154(b) by 114 days.

(21) Appl. No.: 13/145,429

(22) PCT Filed: Dec. 18, 2009

(86) PCT No.: PCT/JP2009/071113
§ 371 (c)(1),
(2), (4) Date: Jul. 20, 2011

(87) PCT Pub. No.: WO2011/074111
PCT Pub. Date: Jun. 23, 2011

(65) Prior Publication Data
US 2011/0276013 A1    Nov. 10, 2011

(51) Int. Cl.
*A61M 5/32* (2006.01)

(52) U.S. Cl.
USPC ............ 604/198; 604/110; 604/192; 604/263

(58) Field of Classification Search
USPC .......... 604/110, 263, 177, 192, 198; 128/919
See application file for complete search history.

(56) References Cited

U.S. PATENT DOCUMENTS

| 4,790,828 A | 12/1988 | Dombrowski et al. | |
|---|---|---|---|
| 4,935,013 A * | 6/1990 | Haber et al. | 604/192 |
| 6,719,731 B2 * | 4/2004 | Parmigiani | 604/192 |
| 2003/0181869 A1 * | 9/2003 | Swenson et al. | 604/263 |
| 2007/0100296 A1 | 5/2007 | Hwang | |

FOREIGN PATENT DOCUMENTS

| JP | 2-26563 | 1/1990 |
|---|---|---|
| JP | 2004-248993 | 9/2004 |
| JP | 2009-513301 | 4/2009 |
| JP | 2009-195552 | 9/2009 |
| WO | 94/11050 | 5/1994 |

OTHER PUBLICATIONS

Supplementary European Search Report dated Jul. 20, 2012 in corresponding European Patent Application No. EP 09852308.8.
International Search Report issued Mar. 30, 2010 in International (PCT) Application No. PCT/JP2009/071113.

* cited by examiner

*Primary Examiner* — Aarti B Berdichevsky
*Assistant Examiner* — Laura Schell
(74) *Attorney, Agent, or Firm* — Wenderoth, Lind & Ponack, L.L.P.

(57) ABSTRACT

To develop a medical needle having a small protecting member that is not separate from a needle and a hub, is not obstructive to the performer during use, and is easy to switch from being in a usable state to being in a protective state.
A pair of wings are pivotally connected to a hub provided at the tail end of a needle, the wings being provided on both sides of the axis of the needle; one or two or more link members are connected to the tip of each of the wings with joints interposed therebetween; the tips of the link members are pivotally connected to a cylindrical protecting member slidably fitted onto the needle; and, when the protecting member is moved toward the tip of the needle, the wings and the link members move in such directions as to become parallel to the needle while the protecting member comes to cover the tip of the needle, whereby the above object is solved.

8 Claims, 8 Drawing Sheets

MEDICAL NEEDLE

The present application is a U.S. National Phase Application pursuant to 35 U.S.C. §371 of International Application No. PCT/JP2009/071113 filed Dec. 18, 2009.

TECHNICAL FIELD

The present invention relates to medical needles used for anesthetization and so forth, and particularly to a medical needle having wings for the convenience of use and having a function of preventing misinsertion thereof after use.

BACKGROUND ART

Medical needles having wings for the convenience of use and having a function of preventing misinsertion thereof after use are disclosed in, for example, PTL 1 and PTL 2 listed below.

The medical needles disclosed therein are each of large size with a cylindrical protecting member (protector) covering the entirety of a needle and a hub. Moreover, the protecting member is provided as a separate body from the needle and the hub and is therefore obstructive to the performer during use.

CITATION LIST

Patent Literature

PTL 1: Japanese Unexamined Patent Application Publication No. 2004-248993
PTL 2: Japanese Unexamined Patent Application Publication No. 2009-195552

SUMMARY OF INVENTION

Technical Problem

It is an object of the present invention to develop a medical needle having a small protecting member that is not separate from a needle and a hub, is not obstructive to the performer during use, and is easy to switch from being in a usable state to being in a protective state.

Solution to Problem

The present invention provides a medical needle characterized in that a pair of wings are pivotally connected to a hub provided at the tail end of a needle, the wings being provided on both sides of the axis of the needle; one or two or more link members are connected to the tip of each of the wings with joints interposed therebetween; the tips of the link members are pivotally connected to a cylindrical protecting member slidably fitted onto the needle; and, when the protecting member is moved toward the tip of the needle, the wings and the link members move in such directions as to become parallel to the needle while the protecting member comes to cover the tip of the needle.

In the present invention, the protecting member does not necessarily cover the entirety of the needle and only covers the tip of the needle. Therefore, the protecting member has a very small size and is not obstructive during use of the needle.

The movement of the protecting member is limited by the wings and the link members, and there is no possibility that the protecting member comes off the needle.

The wings are substantially at right angles to the axis of the needle in a usable state, and the performer can perform an operation by holding the wings. When the protecting member is moved to the tip of the needle and the tip of the needle is protected, the wings and the link members are substantially parallel to the axis of the needle, preventing the protecting member from being moved further.

The present invention is characterized in that the wings also function as members of a link mechanism that limits the movement of the protecting member. This reduces the number of components included in the link mechanism, prevents the link mechanism from being obstructive during use, and reduces costs.

The present invention may also be configured such that the link members each include a first link member having the base end thereof connected to the tip of a corresponding one of the wings with a joint interposed therebetween and a second link member having the base end thereof connected to the tip of the first link member with a joint interposed therebetween and the tip thereof pivotally connected to the protecting member.

The present invention may also be configured such that, when the protecting member is moved to the base end of the needle, the first link member is housed into the wing.

The link members connected to the wings may each include a plurality of members connected to one another in series. By providing each link member in the form of two link members including the first and second link members, the entirety of the first link member can be housed in a corresponding one of the wings. Thus, the link members can be completely prevented from being obstructive during use.

The present invention may also be configured such that each of the wings and a corresponding one of the link members are integrally molded from plastic.

The wings and the link members can be integrally molded from plastic. Thus, the number of components is reduced and the ease of assembling is increased. Consequently, the manufacturing cost can be reduced.

Advantageous Effects of Invention

According to the present invention, since the protecting member is of small size, the protecting member is not obstructive during use. Moreover, the movement of the protecting member is limited by the wings and the link members, and there is no possibility that the protecting member comes off the needle and the hub. The medical needle is easy to switch from being in a usable state to being in a protective state by holding and moving the protecting member with fingers toward the tip of the needle.

DESCRIPTION OF EMBODIMENTS

Embodiment

FIGS. 1 to 8 relate to a medical needle 1 according to an embodiment.

The medical needle 1 includes a needle 2, a hub 3, wings 4, first link members 5, second link members 6, a protecting member 11, and so forth.

The hub 3, which is made of plastic and has a cylindrical shape, is fitted to the tail end of the needle 2. The hub 3 is used in inserting a stylet, an inner needle, a catheter, or the like into the needle or in injecting medical fluid.

A pair of wings 4 are pivotally connected to the hub 3 at pivotal connecting portions 7 in symmetry with respect to the axis of the needle 2. The wings 4 are made of plastic and have a substantially rectangular frame-like shape which defines a cavity, with pin-receiving holes at the base ends thereof. At the pivotal connecting portions 7, pins 3a provided on the hub are axially fitted into the pin-receiving holes of the wings 4.

The tip of each of the wings 4 is connected to the base end of a corresponding one of the first link members 5 with a joint 8 interposed therebetween. The tip of the first link member 5 is connected to the base end of a corresponding one of the second link members 6 with a joint 9 interposed therebetween.

Figure 1:
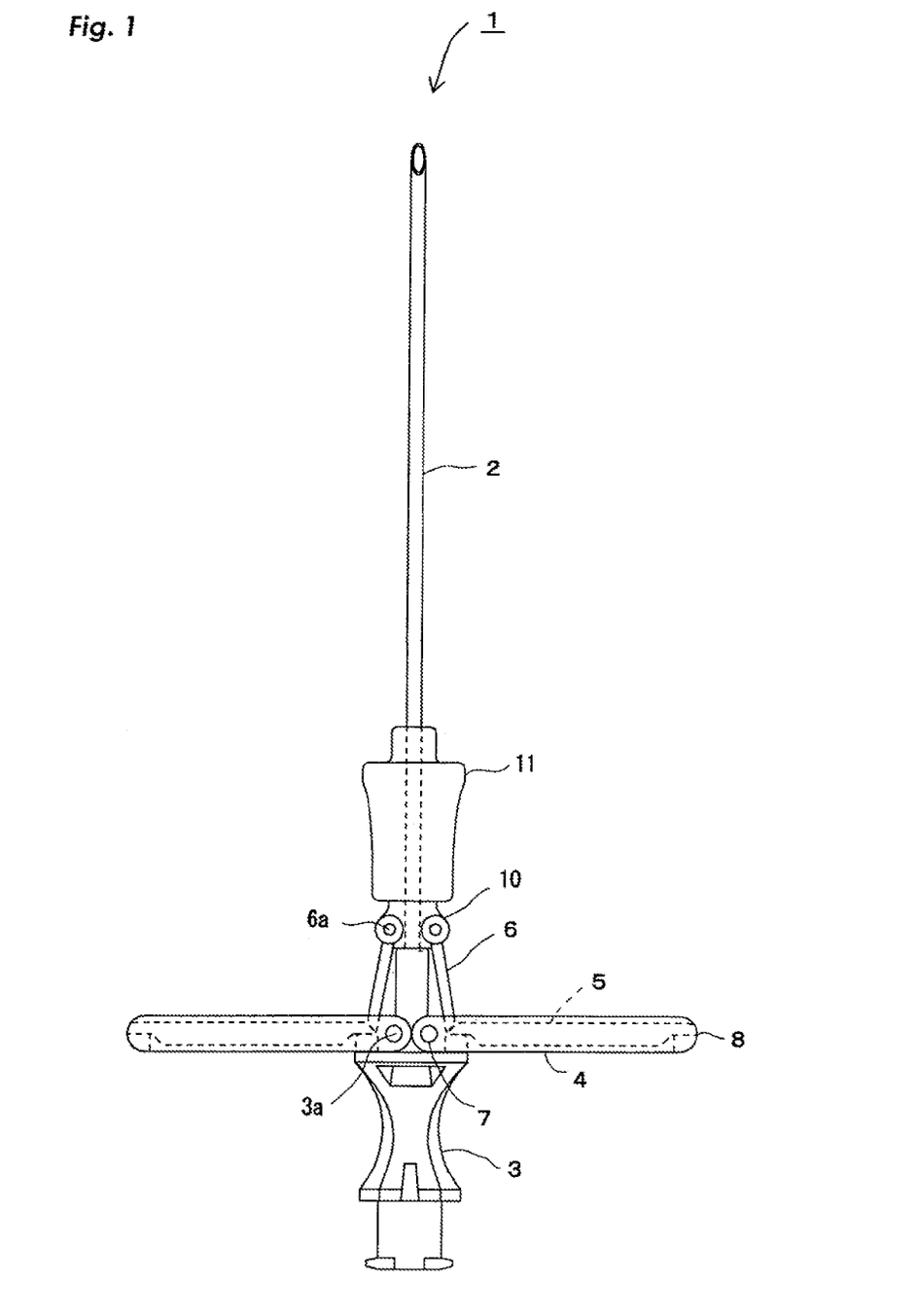
FIG. 1 is a plan view of a medial needle 1 according to an embodiment (in a usable state).
Figure 2:
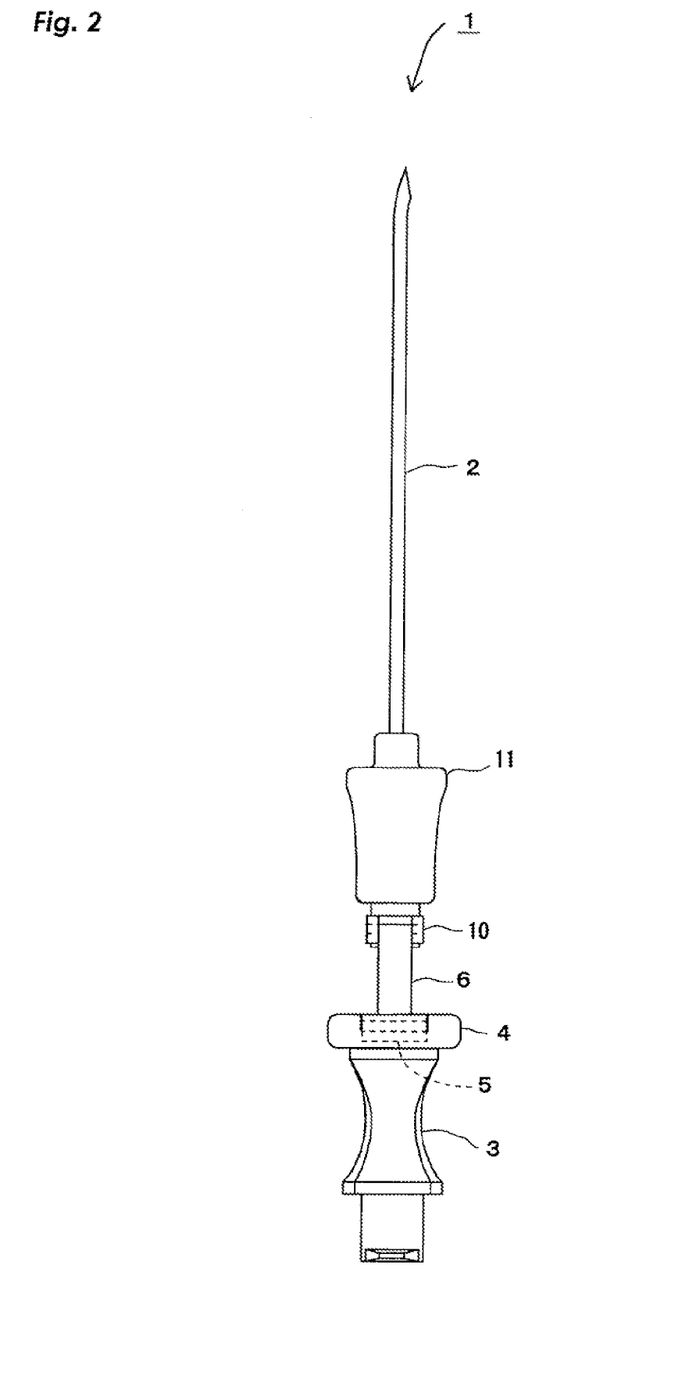
FIG. 2 is a side view of the medial needle 1 (in the usable state).
Figure 3:
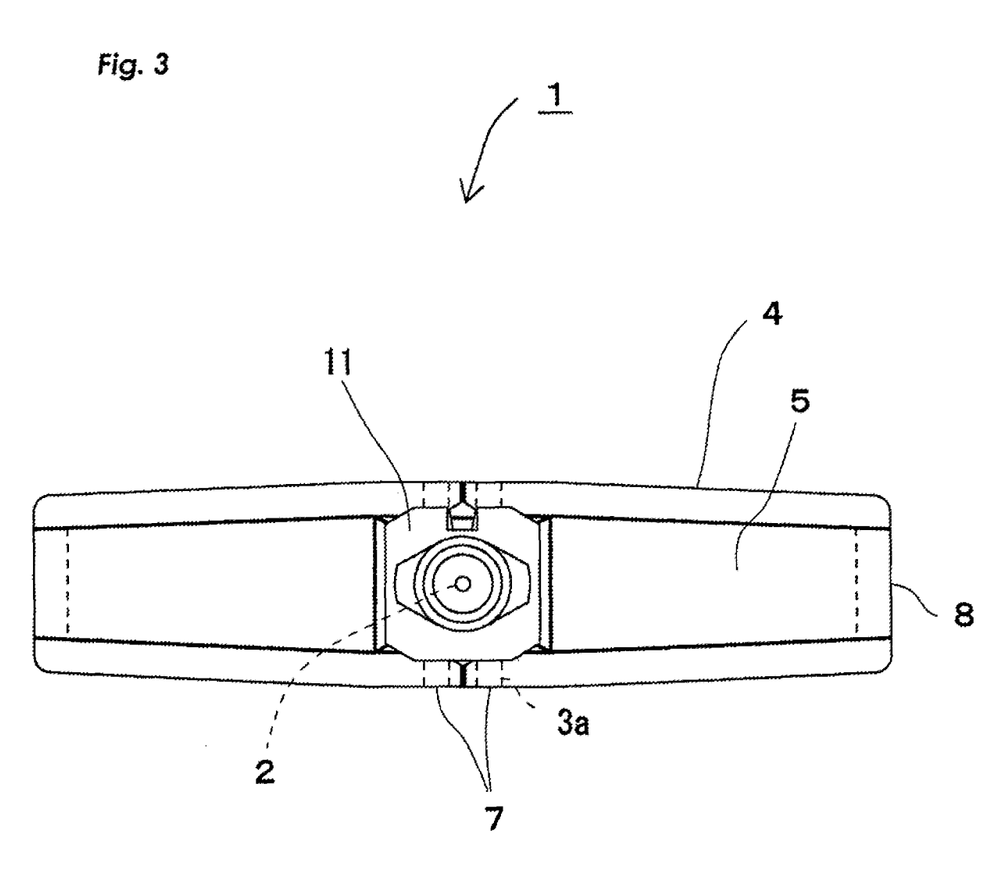
FIG. 3 is a front view of the medial needle (in the usable state).

The wing 4, the first link member 5, and the second link member 6 are integrally molded from plastic. The joints 8 and 9 are flexibly bendable with the elasticity of plastic. As shown in FIGS. 1 to 3, when the medical needle is used, the first link member 5 is entirely housed in the frame-like portion of the wing 4.

In a case where the wing 4, the first link member 5, and the second link member 6 are formed as separate bodies, the joints 8 and 9 may be pivotal connecting structures enabling flexible bending.

The tip of the second link members 6 is pivotally connected to the protecting member 11 at a corresponding one of pivotal connecting portions 10. At the pivotal connecting portion 10, a pin 6a provided at the tip of the second link member 6 is axially fitted into a corresponding one of pin-receiving holes 12c provided at the base end of a main body 12 of the protecting member 11.

Figure 7:
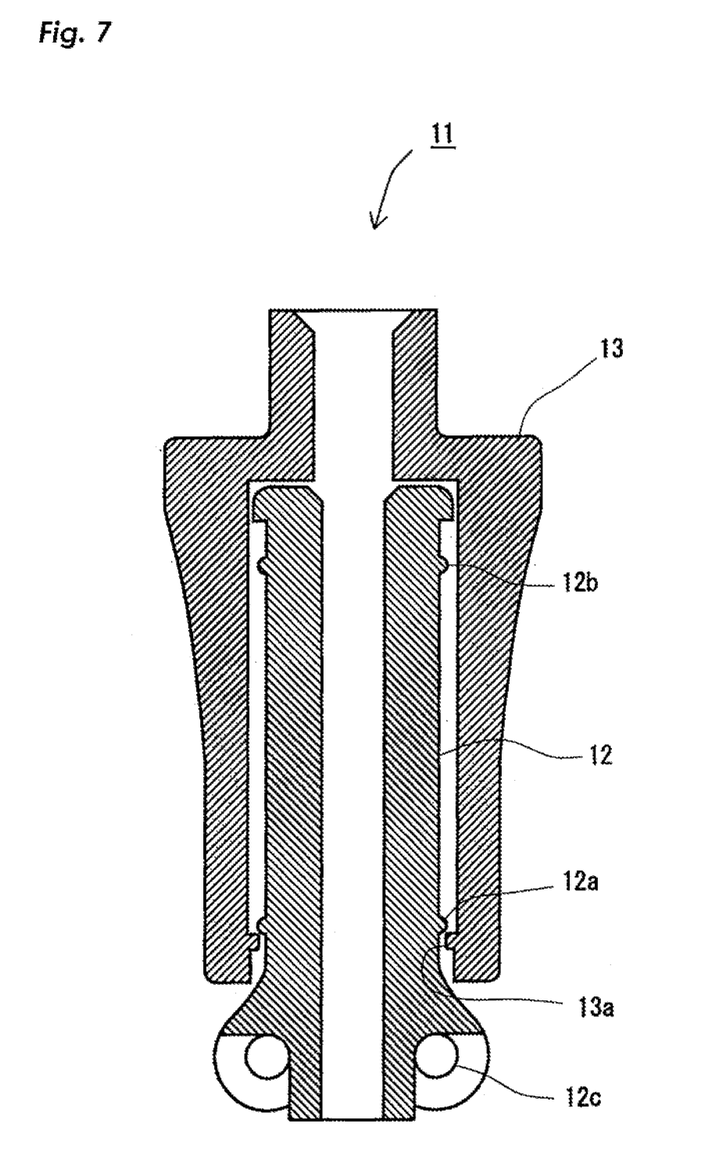
FIG. 7 is a cross-sectional view of the protecting member 11 (in a normal state).
Figure 8:
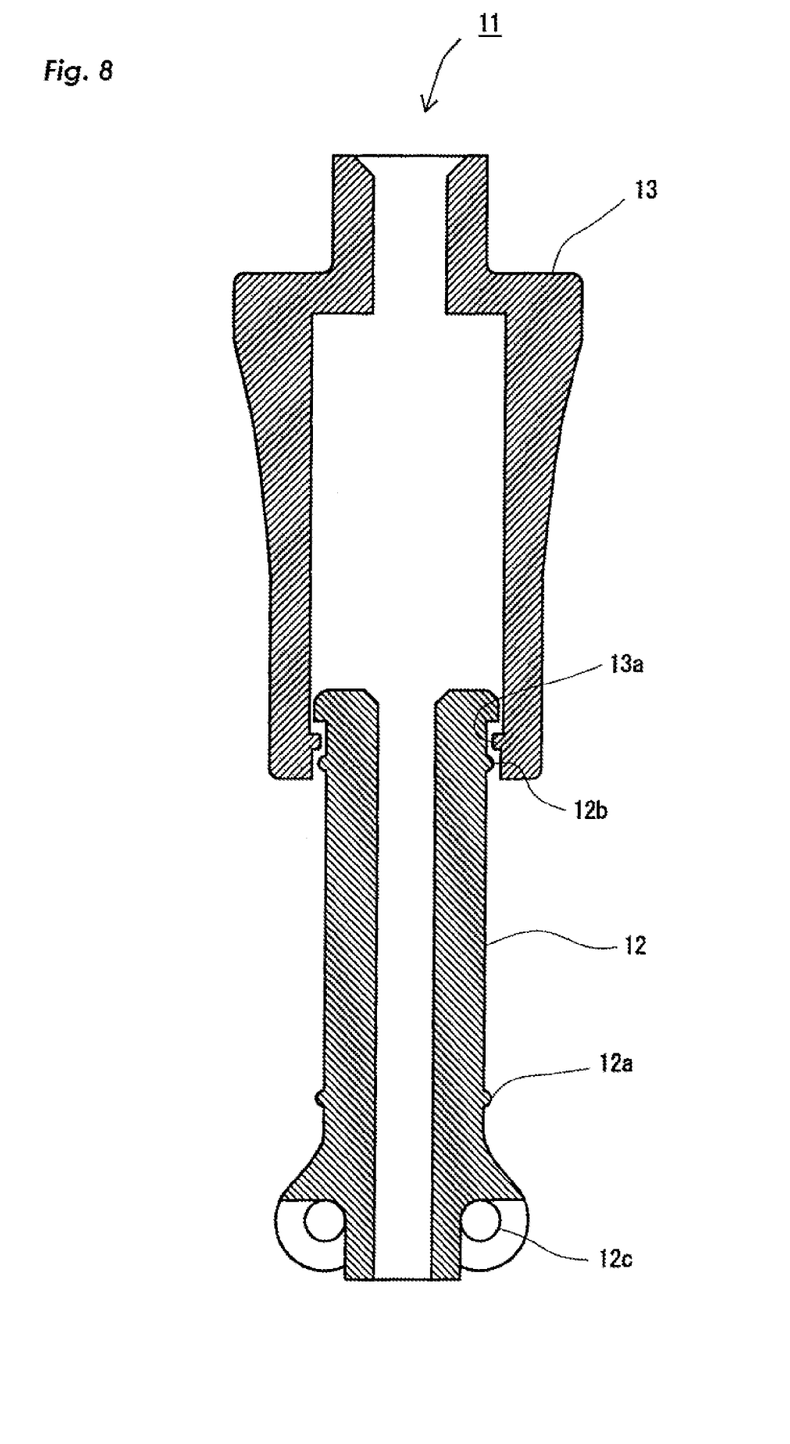
FIG. 8 is a cross-sectional view of the protecting member 11 (in an extended state).

The protecting member 11 is made of plastic and includes the main body 12, having a cylindrical shape, and an extendable portion 13 that are nested together. In a usable state, the protecting member 11 is positioned in a retracted state, as shown in FIG. 7, by a rib 12a of the main body and a rib 13a of the extendable portion 13. In a protective state, the protecting member 11 is positioned in an extended state, as shown in FIG. 8, by a rib 12b of the main body and the rib 13a of the extendable portion 13.

FIGS. 1 to 3 show the usable state, in which the wings 4 are substantially at right angles to the axis of the needle. In this state, the needle is inserted into a human body, and an operation such as insertion of a catheter is performed.

Figure 4:
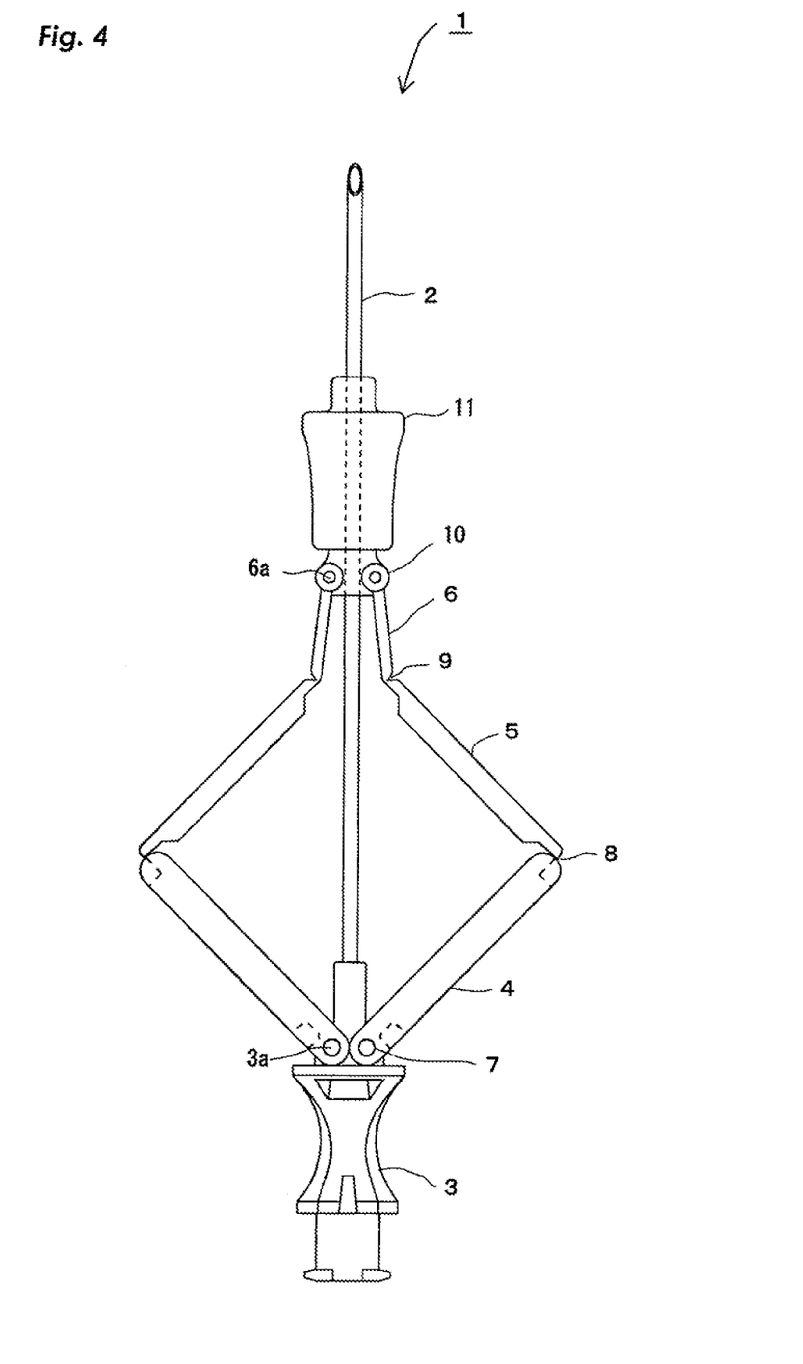
FIG. 4 is a plan view of the medial needle (while a protecting member is being moved).
Figure 5:
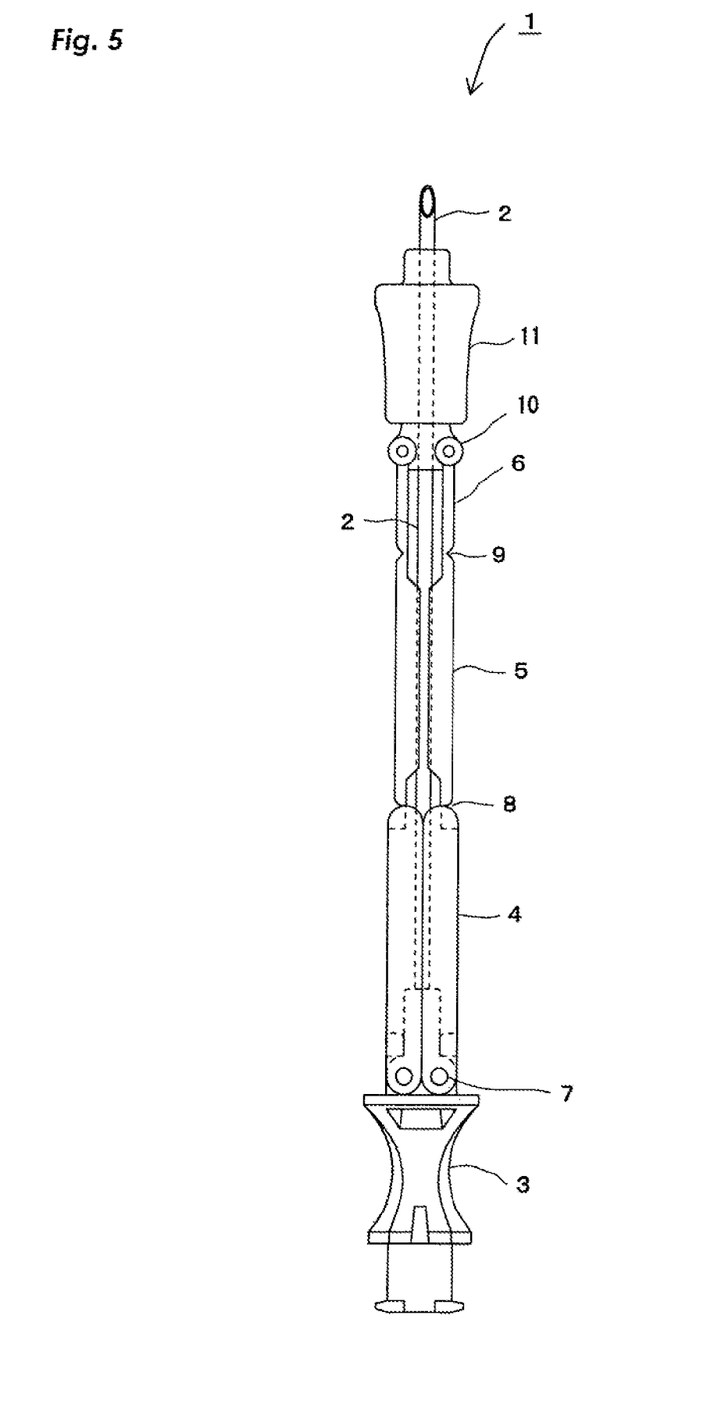
FIG. 5 is a plan view of the medial needle (at the completion of the movement of the protecting member).
Figure 6:
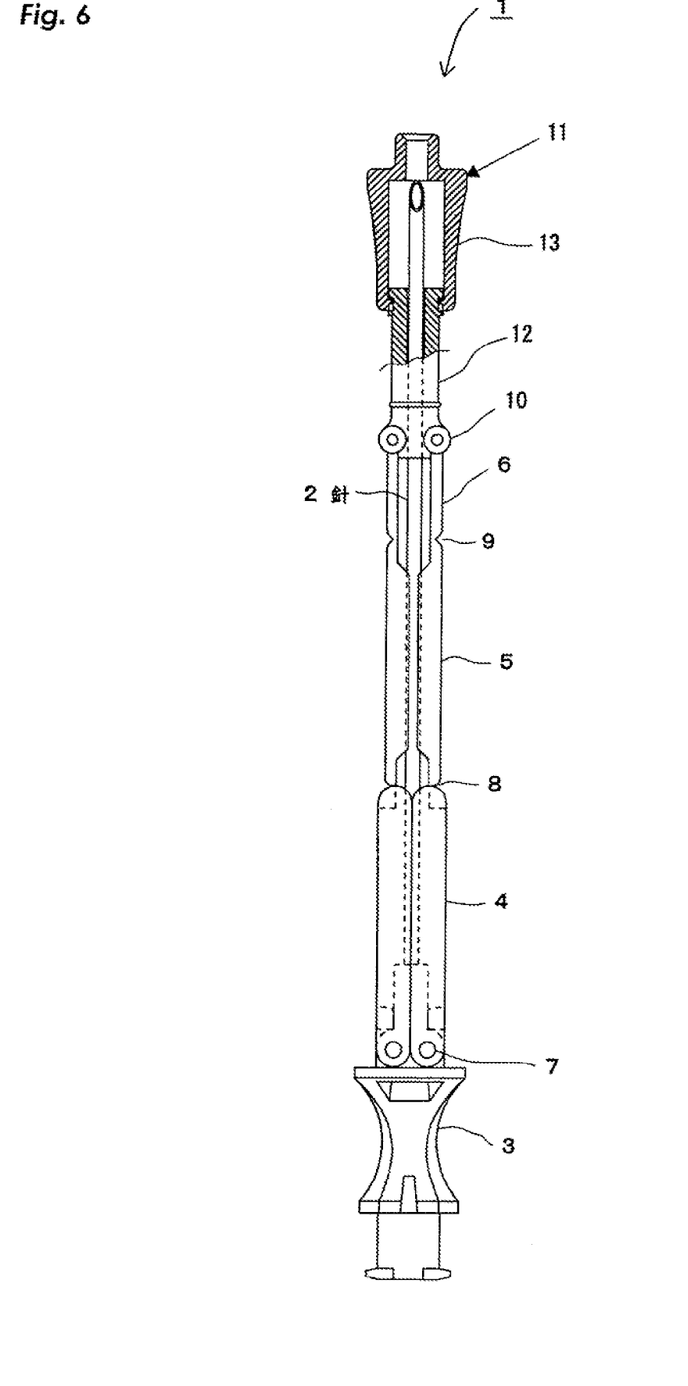
FIG. 6 is a plan view of the medial needle (in a protective state).

After the operation is completed and the medial needle 1 is removed from the human body, the protecting member 11 is held with fingers and is moved toward the tip of the needle 2. FIG. 4 shows a state where the protecting member 11 has been moved to a halfway position of the needle 2. FIG. 5 shows a state where the protecting member 11 has been moved to a position near the tip. In FIG. 5, the wings 4, the first link members 5, and the second link members 6 are substantially parallel to the axis of the needle 2. When the extendable portion 13 of the protecting member 11 in the state shown in FIG. 5 is further moved toward the tip of the needle 2, the extendable portion 13 is extended, as shown in FIG. 8, and completely covers the tip of the needle 2, as shown in FIG. 6.

Thus, misinsertion after use is completely prevented.

The extendable function of the protecting member with a nested structure may not necessarily be provided. That is, the extendable function is not necessary if the protecting member covers the tip of the needle in the state shown in FIG. 5.

REFERENCE SIGNS LIST 1 medical needle
2 needle
3 hub
3a pin
4 wing
5 first link member
6 second link member
6a pin
7 pivotal connecting portion
8 joint
9 joint
10 pivotal connecting portion
11 protecting member
12 main body
12a rib
12b rib
12c pin-receiving hole
13 extendable portion
13a rib

The invention claimed is:

1. A medical needle comprising:
a needle having a tip and a base end opposite to the tip;
a protecting member slidable fitted onto the needle;
a hub disposed at the base end of the needle;
a pair of wings pivotally connected to the hub, the wings being provided on both sides of the axis of the needle;
link members are connected to the tips of the wings, respectively, with the joints disposed between the link members and the wings, and tips of the link members being pivotally connected to the protecting member,
wherein the wings and the link members are configured such that sliding the protecting member toward the tip of the needle moves the wings and the link members in a direction to become parallel to the needle as the protecting member covers the tip of the needle,
wherein the link members each include a first link member and a second link member, the first link member having a base end connected to the tip of a respective one of the wings with a joint interposed therebetween, and the second link member having a base end connected to a tip of the first link member with a joint interposed therebetween and a tip of the second link member being pivotally connected to the protecting member,
wherein each of the wings has a cavity and the respective one of the first link members is housed in the cavity when the protecting member is disposed at the base end of the needle.

2. The medical needle of claim 1, wherein each of the wings and a corresponding one of the link members are integrally molded from plastic.

3. The medical needle of claim 1, wherein the wings and the link members limit the movement of the protective member in a direction from the base end to the tip of the needle.

4. The medical needle of claim 1, wherein the wings and the link members limit the movement of the protective member in a direction from the base end to the tip of the needle, and the wings and link members are configured such that the protective member covers the tip of the needle when the wings and link members are fully extended and parallel to the needle.

5. The medical needle of claim 4, wherein the protecting member includes a main body and an extendable portion which is movable relative to the main body, and the extendable portion extends from the main body to cover the tip of the needle.

6. The medical needle of claim 4, wherein the protecting member includes a main body and an extendable portion which moves relative to the main body in a direction parallel to the needle, and the extendable portion extends from the main body to cover the tip of the needle.

7. The medical needle of claim 1, wherein the protecting member includes a main body and an extendable portion which is movable relative to the main body, and the extendable portion extends from the main body to cover the tip of the needle.

8. The medical needle of claim 1, wherein the protecting member includes a main body and an extendable portion which moves relative to the main body in a direction parallel to the needle, and the extendable portion extends from the main body to cover the tip of the needle.

* * * * *